United States Patent
Novick et al.

(10) Patent No.: US 9,045,559 B2
(45) Date of Patent: Jun. 2, 2015

(54) METHOD FOR SCREENING INHIBITORS OF INTERLEUKIN-32 (IL-32)

(75) Inventors: Daniela Novick, Rehovot (IL); Menachem Rubinstein, Rehovot (IL); Charles A. Dinarello, Boulder, CO (US); Soo-Hyun Kim, Aurora, CO (US)

(73) Assignees: Yeda Research and Development Co. Ltd, Rehovot (IL); The Regents of the University of Colorado, Denver, CO (US)

( * ) Notice: Subject to any disclaimer, the term of this patent is extended or adjusted under 35 U.S.C. 154(b) by 1148 days.

(21) Appl. No.: 12/900,870

(22) Filed: Oct. 8, 2010

(65) Prior Publication Data

US 2011/0044999 A1    Feb. 24, 2011

Related U.S. Application Data

(62) Division of application No. 11/995,216, filed as application No. PCT/IL2006/000798 on Jul. 10, 2006, now abandoned.

(30) Foreign Application Priority Data

Jul. 11, 2005 (IL) .......................................... 169622

(51) Int. Cl.
*C07K 14/54* (2006.01)
*G01N 33/68* (2006.01)

(52) U.S. Cl.
CPC ............ *C07K 14/54* (2013.01); *G01N 33/6869* (2013.01)

(58) Field of Classification Search
None
See application file for complete search history.

(56) References Cited

U.S. PATENT DOCUMENTS

| 4,845,242 A | 7/1989 | Powers et al. |
| 6,342,373 B1 | 1/2002 | Rink et al. |
| 7,560,265 B2 | 7/2009 | Kim et al. |

FOREIGN PATENT DOCUMENTS

| WO | 9015816 A | 12/1990 |
| WO | 9112009 A | 8/1991 |
| WO | 9518797 A | 7/1995 |
| WO | 02087511 A | 11/2002 |
| WO | 2005047478 A2 | 5/2005 |

OTHER PUBLICATIONS

Novick, D. et al., "Proteinase 3 is an IL-32 binding protein." PNAS 103(9):3316-3321, 2006.
McMichael, J. W. et al., "Antimicrobial activity of murine lung cells against *Staphylococcus aureus* is increased in vitro and in vivo after elafin gene transfer." Infection and Immunity 73(6):3609-3617, 2005.
Van Der Geld, Y. M. et al., "In Vitro T Lymphocyte Responses to Proteinase 3 (PR3) and Linear Peptides of PR3 in Patients with Wegener's Granulomatosis (WG)." Clinical and Experimental Immunology 122:504-513, 2000.
Campbell et al. Bioactive Proteinase 3 on the Cell Surface of Human Neutrophils: Quantification, Catalytic Activity, and susceptibility to Inhibition. J. Immunol., 2000, 165: 3366-3374.
Shoda et al, "Rheumaoid arthritis and Interleukin-32", Jpn. J. Clin. Immunol., vol. 30, No. 5, pp. 398-403, 2007. English abstract only.

*Primary Examiner* — Dong Jiang
(74) *Attorney, Agent, or Firm* — Nixon Peabody LLP; David S. Resnick; Leena H. Karttunen Contarino

(57) ABSTRACT

The present invention relates to methods of screening for modulators of interleukin 32 (IL-32), to modulators of IL-32 and to their use.

6 Claims, 8 Drawing Sheets

METHOD FOR SCREENING INHIBITORS OF INTERLEUKIN-32 (IL-32)

CROSS-REFERENCE TO RELATED APPLICATIONS

This application is a Continuation Application of currently pending U.S. application Ser. No. 11/995,216, which is a National Phase Entry Application under 35 U.S.C. §371 of co-pending International Application PCT/IL2006/000798, filed 10 Jul. 2006, which claims benefit of Israeli application No. 169622, filed on 11 Jul. 2005.

FIELD OF THE INVENTION

The present invention relates to methods of screening for modulators of interleukin 32 (IL-32), to modulators of IL-32 and to their use.

BACKGROUND OF THE INVENTION

Interleukin-32 (IL-32) was initially identified in 1992 by Dahl et al. as a cytokine-like molecule named natural killer cell transcript 4 (NK4). Since its initial identification in 1992, NK4 has not been extensively studied and the term NK4 (or NK-4) was assigned also to other unrelated proteins [Kim, 1989; Smart, 1989; Date, 1997]).

Increased gene expression of NK4 in peripheral blood mononuclear cells (PBMC) from patients receiving high-dose IL-2 therapy for malignant melanoma has been reported, but its function has not been determined [Panelli, 2002].

It has been recently reported by Kim et al. (2005) that stimulation of Raw 264.7 macrophage cells with recombinant NK4 induced secretion of large amounts of TNF-α in these cells. Therefore, NK4 was recognized as a pro-inflammatory cytokine and was renamed to IL-32 [Kim, 2005].

The gene encoding IL-32 resides in the human chromosome 16 p13.3. The IL-32 gene contains eight exons. Four IL-32 mRNA splice variant encoding IL-32α, IL-32β, L-32δ and IL-32γ isoforms, were detected in human natural killer (NK) cells, and the IL-32γ isoform was identified to be identical to the transcript previously reported as the NK4 transcript [Kim, 2005]. The IL-32γ transcript, including exons 3 and 4, encodes a protein isoform having 46 additional amino acids at the N terminus. In the IL-32δ transcript the second exon is absent and initiation of translation occurs at an ATG codon present at the third exon. Unlike the other variants, the IL-32α transcript lacks exons 7 and 8 and encodes a protein isoform missing 57 amino acid residues at its C terminus. Out of the four IL-32 transcripts, the IL-32α transcript is the most abundant, hence IL-32α was more extensively characterized. Analysis of the amino acid sequence of the IL-32α isoform revealed three potential N-myristoylation sites and one N-glycosylation site [Kim, 2005].

IL-32α and β were reported to induce secretion of significant amounts of tumor necrosis factor-α (TNF-α) and macrophage inflammatory protein-2 (MIP-2) in a dose-dependent manner from PMA-differentiated THP-1 cells and from mouse Raw cells. Recombinant IL-32-α and β (rIL-32-α and β) were reported to induce IL-8 production in non-differentiated human monocytic THP-1 cells. An Fab fragment of a monoclonal antibody directed against rIL-32β was found to reduce the biological activity of rIL-32α by up to 70% in a dose-dependent manner. At the transcriptional level, the 1.2 KB IL-32 mRNA was detected in several tissues, but was more prominent in immune cells than in non-immune tissues (Kim, 2005).

Human peripheral blood mononuclear cells (PBMC), which contain mostly T cells, produced and secreted IL-32 following stimulation with Con A (inducing mainly T cell stimulation). Production or secretion of IL-32 was not detected following lipopolysaccharides stimulation of PBMC (inducing mainly macrophage stimulation). These results suggest that T cells are the major producers of IL-32. Nevertheless, stimulation of epithelial cell lines with IFN-gamma was found to induce IL-32 production.

The pro inflammatory activity of IL-32 appears to be mediated through degradation of I-κB, leading to activation of NF-κB. However, MAP kinase activation by IL-32α has also been reported [Kim, 2005].

Proteinase 3 (PR-3, also known as myeloblastin, neutrophil PR-3 and Wegener autoantigen) is a granule serine protease produced by neutrophiles/monocytes and is capable of processing multiple biologic substrates [Baggiolini, 1978; Kao, 1988]. PR-3 degrades a variety of extracellular matrix proteins, including elastin, fibronectin, type IV collagen, and laminin and inactivates p65 NF-κB [Preston, 2002]. PR-3 cleaves many pro-hormones and cytokines including angiotensinogen, TGF-β1, IL-1β, IL-8 and the membrane bound TNF-α into their active form [Ramaha, 2002; Csernok, 1996; Coeshott, 1999; Padrines, 1994; Robache-Gallea, 1995]. Indeed, high titers of PR-3 autoantibodies (see below) were found to completely block the cleavage of TNF-α.

PR-3, which appears both in soluble and cell membrane forms, is the major autoantigen in Wegener's granulomatosis (WG). Wegener's granulomatosis is the most common autoimmune necrotizing systemic vasculitis in adults and is manifested mainly in the respiratory tract and kidneys [Lamprecht, 2004; Frosch, 2004].

Autoantibodies to PR-3, known as "Anti-neutrophil cytoplasmic autoantibodies" (ANCA) are a diagnostic hallmark of WG [van Rossum, 2003; Jennette, 1997]. The frequency of the membrane PR-3 (mPR-3)-high phenotype was found to be significantly higher in patients with ANCA-associated vasculitis and in patients with rheumatoid arthritis. Hence, membrane PR-3 expression is a risk factor for vasculitis and rheumatoid arthritis [Witko-Sarsat, 1999]. Expression of PR-3 in the membranes of neutrophil cells is related to relapse in PR-3-anti-neutrophil cytoplasmic autoantibodies (ANCA)-associated vasculitis. Patients with small vessel vasculitis have increased levels of circulating PR-3 protein in their plasma [Ohlsson, 2003]. High levels of PR-3 expression on the membrane of neutrophils is also a WG risk factor and is associated with relapse of WG disease (Rarok A A, Stegeman C A, Limburg P C, Kallenberg C G. J Am Soc Nephrol. 2002 September; 13(9): 2232-8.

Apparently, pathogenesis of WG is induced by the binding of ANCA to PR-3 antigen present on the surface of neutrophils and monocytes. Binding of ANCA to neutrophils and monocytes causes cell activation, respiratory burst and release of toxic oxygen radicals and proteolytic enzymes. The exposure of PR-3 on the cell surface and binding of anti-PR-3 autoantibodies to neutrophils appears to facilitate autoimmunization and amplification of neutrophil-induced vascular inflammation.

Gene expression profiles of peripheral mature neutrophils and monocytes from patients suffering from ANCA diseases manifested in the kidney showed increased levels of transcripts of a group of genes that are normally expressed only in bone marrow precursor cells ("left shift"). PR-3 transcript is included in this group of increased genes and the increase of PR-3 expression correlated with the disease activity and with glomerulonephritis [Muller Kobold, 1998; Yang, 2004; Yang, 2002].

Cystic fibrosis (CF) patients have increased PR-3 mRNA in circulating monocytes at the time of pulmonary exacerbation [Just, 1999]. Surfactant protein D (SP-D) is an important innate host defense molecule present in the lung of CF affected patients, which interacts with CF-associated pathogens [von Bredow, 2003]. SP-D is a target protein for PR-3. Thus, in CF patients the host defense appears to be impaired due to proteolysis of SP-D by PR-3, thereby increasing the incidence of infection of the lung in these patients.

In patients with inflamed gums functional PR-3 was found to be expressed in oral epithelial cells and ANCA was found in the patient's serum. Said epithelial cells expressing functional PR-3 appear to participate in the inflammatory processes of the gums, including gingivitis and periodontitis [Uehara, 2004].

Besides acting on the cell surface and in the extracellular space, PR-3 enters endothelial cells, where it can mimic caspases, for example, by cleaving NF-κB and inducing sustained JNK activation. PR-3 also cleaves and inactivates the major cell cycle inhibitor p21$^{Waf1/Cip1/Sdi1}$. High levels of PR-3 and p21 cleavage product were found in inflamed human tissue taken from Crohn's disease patients and from ulcerative colitis [Pendergraft, 2004].

Dipeptidyl peptidase I (DPPI) is required for the full activation of neutrophil derived serine proteases such as PR-3. PR-3 knockout mice are not available, but DPPI-deficient mice were successfully generated [Adkison, 2002]. The DPPI knockout mice were found to be resistant to arthritis induction by anti-collagen antibodies and did not accumulated neutrophils in their joints. Resistance to arthritis induction correlated with inactivation of neutrophil-derived serine proteases since knockout mice deficient in serine proteases such as neutrophil elastase (−/−)×cathepsin G (−/−) were shown to be also resistant to induction of arthritis by anti-collagen antibodies.

Enzymatically inactive PR-3 fragments generated by deletion of the catalytic triad [Yang, 2001] still maintain several biological activities, including:
(i) down-modulation of DNA synthesis in normal hematopoietic progenitor cells, an effect which can be reversed by granulocyte-macrophage colony stimulating factor (GM-CSF), implying that PR-3 can function as a counterbalance to regulators of proliferation [Skold, 1999].
(ii) Induction of interleukin-8, both at transcriptional and translational levels [Berger, 1996], and
(iii) Induction of apoptosis in human umbilical vein endothelial cells (HUVEC) [Yang, 2001].

As previously mentioned, PR-3 is a serine proteinase and many well-characterized natural and synthetic serine proteinase inhibitors are capable of inactivating PR-3, either reversibly or irreversibly. Several serine proteinase inhibitors were reported to specifically inhibit PR-3. The synthetic inhibitors 7-amino-4-chloro-3-(2-bromoethoxy) isocoumarin and 3,4-dichloroisocoumarin (DCI) exhibited kI values of 4700 and 2600 $M^{-1} \cdot s^{-1}$, respectively [Kam, 1992]. Suramin, a hexasulfonated naphtylurea recently used as an anti-tumor drug, is a potent inhibitor of human neutrophil elastase, cathepsin G, and PR-3. The Ki for PR-3 is $5 \cdot 10^{-7}$ M [Cadene, 1997]. A general class of peptidomimetic agents based on 1,2,5-thiadiazolidin-3-one 1,1-dioxide backbone was described and their sulfone derivatives were found to be time-dependent, potent, and highly efficient irreversible inhibitors of human leukocyte elastase, cathepsin G, and PR-3 [Groutas, 1997]. Such compounds were found to be useful as anti-inflammatory agents (Groutas W C., U.S. Pat. No. 5,550,139 Aug. 27, 1996).

Other proteinase inhibitors consist of polypeptides of various sources. Elafin, a human skin derived peptide that inhibits human leukocyte elastase, was shown to be a potent inhibitor of PR-3, showing an $IC_{50}$ of $9.5 \times 10^{-9}$ M. Potency was found to be more than 100-fold higher as compared with antileukoprotease and eglin C [Wiedow, 1991; Zani, 2004]. MNEI (monocyte/neutrophile elastase inhibitor) is a 42 kDa serpin superfamily member, which efficiently inhibits proteases with elastase- and chymotrypsin-like specificities. MNEI rapidly inhibited PR-3 at a rate $>10^7$ $M^{-1} \cdot s^{-1}$ [Cooley, 2001]. A bioengineered serpin (LEX032) was found to be a time-dependent inhibitor of PR-3, forming a highly stable enzyme-inhibitor complex (Ki 12 nM) [Groutas, 1997]. Thus, many serine proteinase inhibitors were specifically shown to inhibit PR-3.

SUMMARY OF THE INVENTION

The present invention relates to a method of screening for a modulator of interleukin 32 (IL-32) activity based on the binding of IL-32 to PR-3, which comprises determining the binding of IL-32 to PR-3 in the presence of a candidate modulator, comparing the level of said binding to the level of binding of IL-32 to PR-3 in the absence of said candidate modulator, and selecting a modulator capable of inhibiting or enhancing said binding.

In an embodiment of the invention, said binding of IL-32 to PR-3 is measured by surface plasmon resonance.

In one embodiment of the invention, said modulator inhibits the binding of IL-32 to PR-3.

In a further embodiment of the invention, the modulator is an inhibitor of IL-32 activity, preferably an inhibitor of the inflammatory activity of IL-32.

In another embodiment of the invention, said modulator enhances the binding of IL-32 to PR-3 and enhances the activity of IL-32.

In yet another embodiment of the invention the modulator is a fragment of PR-3, which binds to IL-32, but is not capable of cleaving it.

The present invention provides a method of screening for an inhibitor of interleukin 32 (IL-32) activity based on the proteolytic activity of PR-3 on IL32, which comprises determining the proteolysis of IL-32 by PR-3 in the presence of a candidate inhibitor and selecting an inhibitor capable of inhibiting the appearance of an IL-32 fragment generated by the proteolityc activity of PR-3 or the disappearance of the intact IL-32.

In one embodiment of the invention, said inhibitor inhibits the inflammatory activity of IL-32.

In another embodiment of the invention, said IL-32 fragment is of about 16 kDa or about 13 kDa.

In addition the invention provides a method of screening for an inhibitor of interleukin 32 (IL-32) activity based on the enhancement of IL-32-mediated cytokine secretion by PR-3 in an IL-32 responsive cell, which comprises contacting IL-32 and PR-3 with an IL-32 responsive cell in the presence of a candidate inhibitor, determining the concentration of a cytokine in the culture medium of said cell, comparing to the concentration of said cytokine in the culture medium of said cell in the absence of said candidate inhibitor, and selecting for an inhibitor capable of inhibiting said cytokine secretion.

In one embodiment of the invention, said inhibitor inhibits the inflammatory activity of IL-32.

In another embodiment of the invention, the IL-32 responsive cell is a T cell or a macrophage cell.

In a further embodiment of the invention, the cytokine is selected from the group consisting of TNF, IL-8 and MIP-2.

The present invention also provides a method of screening for a modulator of the activity of interleukin 32 (IL-32) or of the activity of a fragment thereof, which comprises stimulating an IL-32-responsive cell with IL-32, or with a fragment thereof in the presence of a candidate modulator, determining the concentration of a cytokine secreted into the culture medium of said cell, comparing to the concentration of said cytokine secreted into the culture medium of said cell in the absence of said candidate modulator and selecting a modulator capable of inhibiting or enhancing secretion of said cytokine from said cell.

In one embodiment of the invention, the IL-32 fragment is the fragment of about 16 kDa generated by the proteolytic activity of PR-3.

In another embodiment of the invention, the IL-32 fragment is the fragment of about 13 kDa generated by the proteolytic activity of PR-3.

In a further embodiment of the invention, IL-32 responsive cell is a T cell or a macrophage cell.

In a still further embodiment of the invention, said candidate modulator is selected from the group consisting of the inhibitors and enhancers selected by the methods of the invention.

In a still further embodiment of the invention, the modulator is an inhibitor of the inflammatory activity of IL-32.

The present invention provides modulators of IL-32 activity, such as inhibitors of IL-32 inflammatory activity, selected by the methods of screening according to the invention.

In one embodiment, the invention provides an enhancer of IL-32 activity, selected by the screening methods of the invention.

In one aspect, the invention provides the use of an inhibitor of PR-3 in the manufacture of a medicament for the treatment of a disease which is caused or exacerbated by upregulated production and/or secretion of IL-32 or of a fragment thereof from cells that express it in a mammal, including a human.

In one embodiment of the invention, the disease is caused or exacerbated by production and/or secretion of a fragment of IL-32.

In another embodiment of the invention, the IL-32 fragment is of about 16 kDa and is generated by the proteolytic activity of PR-3.

In a further embodiment of the invention, the IL-32 fragment is of about 13 kDa and is generated by the proteolytic activity of PR-3.

In a still further embodiment of the invention, the cells that express IL-32 or a fragment thereof are epithelial cells.

In a yet further embodiment of the invention, the inhibitor of PR-3 is selected from the group consisting of isocoumarin, dichloroisocoumarin, suramin, hexasulfonated naphtylurea, peptidomimetic agents based on 1,2,5-thiadiazolidin-3-one 1,1-dioxide backbone and their sulfone derivatives, proteinase inhibitor, elafin, antileukoprotease eglin C, MNEI (monocyte/neutrophile elastase inhibitor), the bioengineered serpin LEX032, and a neutralizing anti-PR-3 antibody.

In another aspect, the invention teaches the use of an enhancer or inhibitor of IL-32 screened according to the methods of the invention in the manufacture of a medicament for the treatment of a disease which is caused or exacerbated by unregulated production or secretion of IL-32 or of a fragment thereof from cells that express it in a mammal, including a human.

In one embodiment of the invention, the disease is caused or exacerbated by unregulated production and/or secretion of a fragment of IL-32.

In another embodiment of the invention, the IL-32 fragment is of about 16 kDa and is generated by the proteolytic activity of PR-3.

In a further embodiment of the invention, the IL-32 fragment is of about 13 kDa and is generated by the proteolytic activity of PR-3.

In a yet further embodiment, the modulator is an inhibitor selected by the screening method of the invention.

In a yet further embodiment, the production or secretion of IL-32 or of a fragment thereof from cells that express it is upregulated.

In a yet further embodiment, the cells that express IL-32 or a fragment thereof are epithelial cells.

In a yet further embodiment, the disease is an inflammatory disease.

In a further aspect, the invention relates to a method for treating a disease which is caused or exacerbated by upregulated production and/or secretion of IL-32 or of a fragment thereof from cells that express it in a mammal, including a human, which comprises administering to such mammal in need an effective amount of a PR-3 inhibitor.

In one embodiment of the invention, the disease is caused or exacerbated by unregulated production and/or secretion of a fragment of IL-32.

In another embodiment of the invention, the IL-32 fragment is of about 16 kDa and is generated by the proteolytic activity of PR-3.

In a still further embodiment of the invention, the IL-32 fragment is of about 13 kDa and is generated by the proteolytic activity of PR-3.

In a still further embodiment of the invention, the cells that express IL-32 or a fragment thereof are epithelial cells.

In a still further embodiment of the invention, the PR-3 inhibitor is selected from the group consisting of isocoumarin, dichloroisocoumarin, suramin, hexasulfonated naphtylurea, peptidomimetic agents based on 1,2,5-thiadiazolidin-3-one 1,1-dioxide backbone and their sulfone derivatives, proteinase inhibitor, elafin, antileukoprotease eglin C, MNEI (monocyte/neutrophile elastase inhibitor), the bioengineered serpin LEX032, and a neutralizing anti-PR-3 antibody.

In a still further aspect, the invention relates to a method for treating a disease which is caused or exacerbated by unregulated production and/or secretion of IL-32 or of a fragment thereof from cells that express it in a mammal, including a human, which comprises administering to such mammal in need an effective amount of a modulator selected according to any one of the screening methods of the invention.

In one embodiment of the invention, the disease is caused or exacerbated by upregulated production and/or secretion of a fragment of IL-32.

In another embodiment of the invention, the cells that express IL-32 are epithelial cells.

In a still further embodiment of the invention, the IL-32 fragment is of about 16 kDa or 13 kDa and is generated by the proteolytic activity of PR-3.

The invention also provides a polypeptide fragment of IL-32, obtained by the proteolysis of IL-32 by PR-3, such as the IL-32 fragment consisting of about 16 kDa or of about 13 kDa or, a mutein, fusion protein, functional derivative, a circularly permuted derivative, or active fraction thereof.

In addition, the invention provides a pharmaceutical composition comprising a polypeptide fragment of IL-32 obtained by the proteolysis of IL-32 by PR-3, such as the IL-32 fragment consisting of about 16 kDa or the IL-32 fragment consisting of about 13 kDa or, a mutein, fusion protein, functional derivative, a circularly permuted derivative, or active fraction thereof and a pharmaceutically acceptable carrier.

Also, in one embodiment the invention provides a polypeptide fragment of IL-32 of SEQ ID NO: 1 or, a mutein, fusion protein, functional derivative, a circularly permuted derivative, or active fraction thereof.

In another embodiment, the invention provides a polypeptide fragment of IL-32 of SEQ ID NO: 2 or, a mutein, fusion protein, functional derivative, a circularly permuted derivative, or active fraction thereof.

In a further embodiment, the invention provides a pharmaceutical composition comprising polypeptide fragment of IL-32 of SEQ ID NO: 1, of SEQ ID NO: 2 or, a mutein, fusion protein, functional derivative, a circularly permuted derivative, or active fraction thereof and a pharmaceutically acceptable carrier, for example for enhancing host immune responses against pathogenic agents or cancer.

BRIEF DESCRIPTION OF THE FIGURES

FIG. 2 A. IL-32 (20 µg/ml) in acetate buffer pH 4.6) was immobilized to a single channel of a BIAcore chip as recommended by the manufacturer (Amersham Pharmacia, Uppsala Sweden). Aliquots of elution fraction 3 from the IL-32 affinity column were brought to a concentration of 10, 20, 30, 40 and 80 nM (binding curves from bottom to top, respectively) and analyzed by the BIAcore system. The binding data gave a kD of $2.65 \times 10^{-8}$ M. FIG. 2 B. The same analysis was done with PR-3 that was inactivated by phenyl methyl sulfonyl fluoride (PMSF). The resulting kD was $7.9 \times 10^{-8}$ M.

DETAILED DESCRIPTION OF THE INVENTION

The present invention relates to methods of screening (or identification or selection) for a modulator of the activity of interleukin 32 (IL-32), based on our findings that PR-3 binds IL-32 causes IL-32 proteolysis and the proteolytic fragments generated by the action of PR-3 have enhanced activity.

In addition, the present invention relates to the modulators of IL-32 activity identified by said method of screening and to the use of said modulators in a disease which is caused or exacerbated by the unregulated production and/or secretion of IL-32 or of a fragment thereof.

The invention also relates to inhibitors of IL-32 activity which are fragments of PR-3 which bind to, but are incapable of cleaving, IL-32.

Cytokines normally serve to enhance defense. However, when acting in excess, they may cause great damage, not lesser than that which pathogens can cause. In fact, in many diseases unwarranted effects of cytokines constitute a major pathogenic cause. Upregulated production and/or secretion of IL-32 or a fragment thereof may cause an inflammatory disease or may exacerbate an inflammatory disease. An inhibitor of IL-32 activity is desired to inhibit inflammatory diseases caused or exacerbated by upregulation of IL-32 production and/or secretion. Down-regulated production and/or secretion of IL-32 or a fragment thereof may impair host defense, thereby increasing the incidence of infections and cancer. An enhancer of IL-32 activity is desired to inhibit infections and cancer caused or exacerbated by downregulation of IL-32 production and/or secretion. The present invention is based on our findings that PR-3 binds to IL-32 with a high affinity and degrades IL-32 into 13 and 16 kDa fragments, which exhibit enhanced biological activity as compared to the biological activity of intact IL-32.

As is illustrated in the Examples section which follows, we have established that PR-3 plays a crucial role in activation of IL-32.

Figure 1:
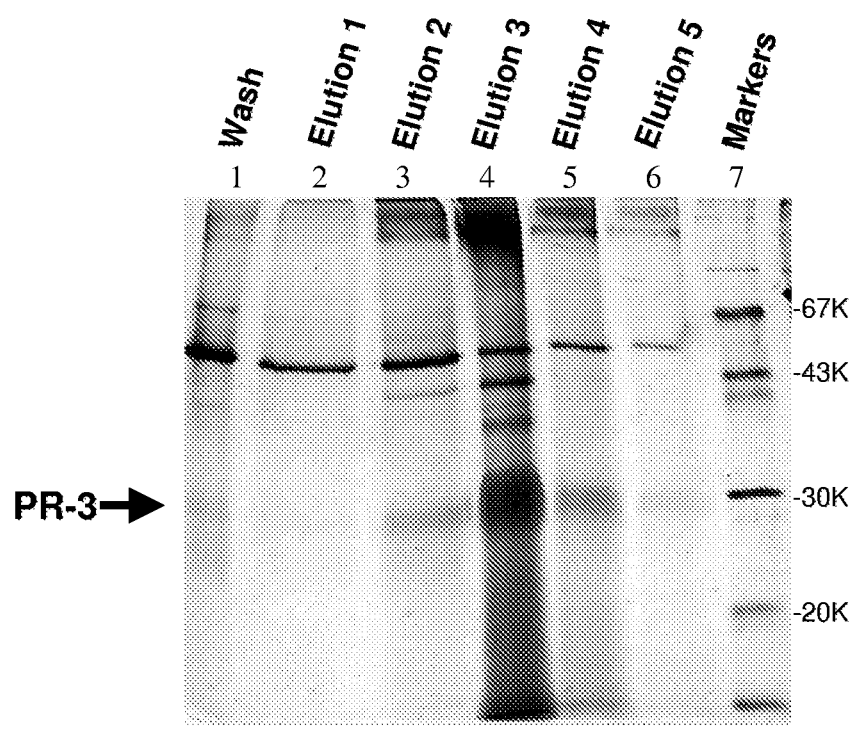
FIG. 1 shows fractions of urinary proteins eluted from the IL-32 immobilized affinity chromatography column resolved in SDS-PAGE. IL-32 was immobilized on an Affigel 15 resin and concentrated urinary proteins from 500 L of urine were passed on the resin; the resin was washed and resin-bound proteins were eluted by a pH 2.2 buffer in 1 ml fractions. Aliquots (60 µl) from the various fractions were resolved in SDS-PAGE (12% acrylamide; non-reducing conditions) and the gel was silver-stained. Lane 1 is the wash fraction; lanes 2-6 are the elution fractions 1 to 5, respectively and lane 7 shows the molecular mass markers, indicated on the right side (in kDa). The arrow in the figure shows an IL-32-binding protein of 30±2 kDa that eluted mainly in fraction 3 and was identified as PR-3.

Briefly, we concentrated and loaded on a column consisting of human IL-32 bound to agarose, crude human urinary proteins. We eluted the column-bound proteins by lowering the column pH and analyzed the eluted proteins by SDS-PAGE (10% acrylamide). A protein band of 28-32 kDa further identified as the neutrophil-derived serine protease PR-3 (as described in Example 1 below) was specifically enriched in one of the eluted fractions (FIG. 1 elution fraction 3).

We found that PR-3 binds to IL-32 with high affinity (Kd of about $2.65 \times 10^{-8}$ M with the urinary PR-3 and Kd of about $1.20 \times 10^{-8}$ M with the commercial PR-3, see Example 2). The binding affinity of PR-3 to IL-32 decreased very little after pre-incubating PR-3 with phenyl methyl sulfonyl fluoride (PMSF), indicating that binding of IL-32 to PR-3 is not dependent on the enzymatic activity of the latter.

We found that PR-3 cleaved IL-32 (of about 20 kDa) into fragments of about 13 kDa (SEQ ID NO: 1) and 16 kDa (SEQ ID NO: 2).

For the purpose of the present description the expression "biological activity of IL-32" refers inter alia to at least one of the following biological properties:
(i) induction of MIP-2, (ii) induction of TNF, and (iii) induction of IL-8.

Therefore, based on our results, modulating the binding of IL-32 to PR-3 (or formation of the IL-32-PR-3 complex) will modulate, namely enhance or inhibit, the activity of IL-32. As used herein, the expression "inhibiting the activity of IL-32" means the capability of an inhibitor to inhibit any IL-32 activity in addition to blocking, e.g. partial inhibition, or the like.

The invention provides a method of identifying a modulator molecule, the method comprising identifying a molecule capable of enhancing or inhibiting the binding of PR-3 to IL-32 (or PR-3-IL-3 complex formation), said molecule being the modulator.

In one embodiment, the present invention relates to a method of screening for a modulator of interleukin 32 (IL-32) activity based on the binding of IL-32 to PR-3, which comprises determining the binding of IL-32 to PR-3 in the presence of a candidate modulator, comparing to the binding of IL-32 to PR-3 in the absence of said candidate modulator, and selecting (or identifying) a modulator capable of inhibiting or enhancing said binding.

In one embodiment the candidate modulator is an organic molecule which may be designed by combinatorial chemistry.

The term "IL-32" according to the invention, includes all the IL-32 isoforms such as IL-32 α, IL-32 β, IL-32 γ and IL-32 δ.

The term "modulator of IL-32 activity" means an inhibitor or an enhancer of IL-32 activity.

As used herein, the expression "binding to IL-32" means the capability of PR-3 to bind IL-32, e.g. as evidenced by PR-3 binding to IL32 when affinity purified as in Example 1 or when tested in BIAcore as in Example 3.

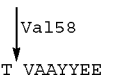

MCFPKVLSDDMKKLKARMHQAIERFYDKMQNAESGRGQVMSSLAELEDDFKEGYLET VAAYYEE
QHPELTPLLEKERDGLRCRGNRSPVPDVEDPATEEPGESFCDKSYGAPRGDKEELTPQKCSEPQSSK

PR-3 cleaves IL-32 between Thr (57) and Val (58):YLET (57) V(58) AAY.

The 13 kDa sequence is supposed to be the N-terminal fragment of IL-32: MCFPKVLSDDMKKLKARM-HQAIERFYDKMQNAESGRGQVMSS-LAELEDDFKEGYLET (SEQ ID NO:1) and the 16 KDa sequence the C-terminal fragment: VAAYYEEQHPELT-PLLEKERDGLRCRGNRSPVPDVEDPA-TEEPGESFCDKSYGAPR GDKEELTPQKCSEPQSSK (SEQ ID NO: 2).

We showed that the IL-32 protein (of about 20 kDa) disappeared after one min incubation with commercial PR-3, concomitantly with the generation of the 13 kDa (SEQ ID NO: 1) and 16 kDa (SEQ ID NO: 2) fragments. Pretreatment of PR-3 with PMSF completely blocked the cleavage of IL-32.

To our surprise we found that the proteolytic fragments of IL-32, of 13 kDa (SEQ ID NO: 1) and 16 kDa (SEQ ID NO: 2), had enhanced biological activity compared to the intact IL-32 protein (as demonstrated in Example 8). The cleavage of IL-32 and the consequent enhancement of the biological activity were both blocked by the action of PMSF.

As mentioned, cytokines normally serve to enhance defense. However, when acting in excess, they may cause great damage, not lesser than that which pathogens can cause. In fact, in many diseases unwarranted effects of cytokines constitute a major pathogenic cause. IL-32 acting in excess may cause excessive function of TNF and inflammation. In a further embodiment of the present invention, the modulator is an inhibitor of the inflammatory activity of IL-32.

Deficiency of IL-32 may impair host defense, thereby increasing the incidence of infections and cancer. In a further embodiment of the present invention, the modulator is an enhancer of the activity of IL-32.

Based on our results, inhibiting proteolysis of IL-32 by PR-3 will result in the inhibition of the activity of IL-32 (As exemplified below with PMSF).

The invention provides a method of identifying a modulator molecule, the method comprising identifying a molecule capable of enhancing or inhibiting the proteolysis of IL-32 by PR-3, said molecule being the modulator.

In one embodiment the invention relates to a method of screening for an inhibitor of IL-32 (IL-32) activity based on the proteolytic activity of PR-3 on IL-32, which comprises determining the proteolysis of IL-32 by PR-3 in the presence of a candidate inhibitor and selecting an inhibitor capable of inhibiting the appearance of an IL-32 fragment generated by the proteolityc activity of PR-3 or the disappearance of the intact IL-32.

In a further embodiment, determining the proteolysis of IL-32 is carried out by monitoring IL-32 fragments generated by PR-3, having molecular weights of about 16 and 13 kDa and/or by monitoring the disappearance of the intact IL-32 of molecular weight of about 20 kDa as exemplified in Examples 5-7.

Based on our results, inhibiting PR-3 will inhibit the biological activity of IL-32 (as exemplified below with PMSF).

In accordance with another embodiment of the present invention, fragments of PR-3, which can be obtained by cleavage of PR-3 by any known method, which bind IL-32, but are not capable of cleaving it, may be employed to abolish the enhancing function of PR-3 on the biological activity of IL-32 as manifested by the cleaved IL-32.

In accordance with the invention PR-3 is cleaved by CNBr, or trypsin and the resulting fragments of PR-3 are checked for affinity to IL-32 by BIACORE and compared to the affinity of intact PR-3. Fragments with high affinity are then further tested for inhibition of the biological activity of IL-32.

The invention provides a method of identifying a modulator molecule, the method comprising identifying a molecule capable of enhancing or inhibiting the biological activity of IL-32 enhanced by PR-3, wherein the biological activity is manifested by secretion of a cytokine such as IL-8, TNF and MIP-4 by IL-32 responsive cells, said molecule being the modulator.

In one embodiment, the invention relates to a method of screening for an inhibitor of interleukin 32 (IL-32) activity based on the enhancement of IL-32-mediated cytokine secretion by PR-3 in an IL-32 responsive cell, which comprises contacting IL-32 and PR-3 with an IL-32 responsive cell in the presence of a candidate inhibitor, determining the concentration of a cytokine in the culture medium of said cell, comparing to the concentration of said cytokine in the culture medium of said cell in the absence of said candidate inhibitor, and selecting for an inhibitor capable of inhibiting said cytokine secretion.

The invention provides a method of identifying a modulator molecule, the method comprising identifying a molecule capable of enhancing or inhibiting the activity of IL-32 or a molecule capable of enhancing or inhibiting the activity or the production of IL-32 13 kDa (SEQ ID NO: 1) and 16 kDa (SEQ ID NO: 2) fragments, said molecule being the modulator.

In one embodiment, the present invention relates to a method of screening for a modulator of the activity of interleukin 32 (IL-32) or a molecule capable of enhancing or inhibiting the activity or production of fragment thereof, which comprises stimulating an IL-32-responsive cell with IL-32, or with a fragment thereof in the presence of a candidate modulator, determining the concentration of a cytokine secreted into the culture medium of said cell, comparing to the concentration of said cytokine secreted into the culture medium of said cell in the absence of said candidate modulator and selecting a modulator capable of inhibiting or enhancing secretion of said cytokine from said cell.

As used herein, the expression "enhancement of IL-32-mediated cytokine secretion by PR-3 "means the capability of PR-3 to enhance IL-32 mediated cytokine secretion in an IL-32 responsive cell, for example, as evidenced by enhancement of IL-8 or MIP-2 secretion stimulated by IL32 incubated with PR-3 (as exemplified in Example 8).

In one embodiment, the present invention relates to modulators of IL-32 found by the method of the present invention and to their use in the manufacture of a medicament for the treatment of a disease which is caused or exacerbated by unregulated production or secretion of IL-32 or of a fragment thereof from cells that express it in a mammal, including a human.

In a further embodiment, the present invention relates to the use of a modulator of PR-3 in the manufacture of a medicament for the treatment of a disease, which is caused or exacerbated by unregulated production and/or secretion of IL-32 or of a fragment thereof from cells that express it in a mammal, including a human.

Our results show that inhibitors of the present invention, such as inhibitors of PR-3, inhibitors of binding of PR-3 to IL-32, inhibitors of IL-32 proteolysis by PR-3 (exemplified below with PMSF) and inhibitors of the biological activity of IL-32 identified by the methods of screening of the present invention may find use as inhibitors of IL-32 activity for example, in diseases in which endogenous production or exogenous administration of IL-32 is the cause of the disease or exacerbates the situation of the patient.

In one embodiment of the invention, an inhibitor of IL-32 activity identified by the method of screening of the present invention, is used in a disease, which is caused or exacerbated, by the increased production and/or secretion of IL-32 such as inflammation.

The terms "inflammation", "inflammatory diseases", "inflammatory condition" or "inflammatory process" are meant as physiological or pathological conditions, which are accompanied by an inflammatory response. Such conditions include, but are not limited to, sepsis, ischemia-reperfusion injury, Crohn's disease, rheumatoid arthritis, multiple sclerosis, cardiomyopathic disease, colitis, infectious meningitis, encephalitis, acute respiratory distress syndrome, Wegener's granulomatosis, atherosclerosis, organ/tissue transplant rejection (such as skin, kidney, heart, lung, liver, bone marrow, cornea, pancreas, small bowel), dermatitis, stroke, traumatic brain injury, psoriasis and lupus.

The present invention provides methods for treating a disease which is caused or exacerbated by unregulated production and/or secretion of IL-32 or of a fragment thereof in a cell that express it, such as T cells and endothelial cells, in a mammal, including a human, which comprises administering to such mammal in need an effective amount of PR-3 inhibitor.

The term "treatment" or "treating" is intended to include the administration of the compound of the invention to a subject for purposes which may include prophylaxis, amelioration, prevention or cure of caused or exacerbated by unregulated IL-32 activity. Such treatment need not necessarily completely ameliorate the inflammatory response or other responses related to the specific disorder. Further, such treatment may be used as sole treatment or in conjunction with other traditional treatments for reducing the deleterious effects of the disease, disorder or condition as known to those of skill in the art.

The methods of the invention may be provided as a "preventive" treatment before detection of, for example, an inflammatory state, so as to prevent the disorder from developing in patients at high risk for the same, such as, for example, transplant patients.

The term "cancer" refers to various cancer-associated conditions including metastasis, tumor growth, and angiogenesis.

According to the present invention inhibitors of PR-3 such as PR-3 inhibitor selected from isocoumarin, dichloroisocoumarin, suramin, hexasulfonated naphtylurea, peptidomimetic agents based on 1,2,5-thiadiazolidin-3-one 1,1-dioxide backbone and their sulfone derivatives, proteinase inhibitor, elafin, antileukoprotease eglin C, MNEI (monocyte/neutrophile elastase inhibitor), the bioengineered serpin LEX032, and a neutralizing anti-PR-3 antibody are provided as inhibitors of IL-32 activation and release.

The invention also includes the use of neutralizing antibodies against PR-3 as well as against their muteins, fused proteins, salts, functional derivatives and active fractions. The term "antibody" is meant to include polyclonal antibodies, monoclonal antibodies (MAbs), chimeric antibodies, anti-idiotypic (anti-Id) antibodies to antibodies that can be labeled in soluble or bound form, and humanized antibodies as well as fragments thereof provided by any known technique, such as, but not limited to enzymatic cleavage, peptide synthesis or recombinant techniques.

As mentioned, cytokines normally serve to enhance defense. Although IL-32 acting in excess may cause excessive function of TNF, IL-32 or active fragments thereof at permissive concentrations may serve to enhance host defense.

In one aspect, the invention relates to a polypeptide fragment of IL-32 of about 16 kDa (SEQ ID NO: 2) and to a polypeptide fragment of IL-32 of about 13 kDa (SEQ ID NO: 1), both active and obtained by the proteolytic activity of PR-3.

The invention relates also to the IL-32 16 kDa (SEQ ID NO: 2) polypeptide or, a mutein, fusion protein, functional derivative, a circularly permuted derivative, or active fraction thereof.

The invention relates also to the IL-32 13 kDa (SEQ ID NO: 1) polypeptide or, a mutein, fusion protein, functional derivative, a circularly permuted derivative, or active fraction thereof.

As used herein the term "muteins" refers to analogs of a protein, in which one or more of the amino acid residues of the naturally occurring components of the protein are replaced by different amino acid residues, or are deleted, or one or more amino acid residues are added to the original sequence of the protein, without changing considerably the activity of the resulting products as compared with the original protein. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes the protein, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12° 20-° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of the polypeptides of the invention, such as to have substantially similar, or even better, activity to the polypeptides of the invention. For example, one characteristic activity of IL-32 is its capability of inducing secretion of TNF in responsive cells. An ELISA type assay for measuring the binding of TNF are described in the art. As long as the mutein has substantial activity of the polypeptide of the invention, it can be considered to have substantially similar activity to the polypeptide of the invention. Thus, it can be determined whether any given mutein has at least substantially the same activity as the polypeptide of the invention by means of routine experimentation comprising subjecting such a mutein, e.g., to simple assays to determine whether or not it induces secretion of a cytokine such as TNF, IL-8 or MIP-2 in IL-32 responsive cells.

In a preferred embodiment, any such mutein has at least 40% identity or homology with the amino acid sequence of the polypeptide of the invention. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino cid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1): 387-95.), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21; 91(2): 379-80 and J Mol. Biol. 1981 Mar. 25; 147(1): 195-7. 1981) and finds the best single region of similarity between two sequences. Other programs for determining identity and/or similarity between sequences are also known in the art, for instance the BLAST family of programs (Altschul S F et al, 1990 J Mol. Biol. 1990 Oct. 5; 215(3): 403-10, Proc Natl Acad Sci USA. 1990 July; 87(14): 5509-13, Altschul S F et al, Nucleic Acids Res. 1997 Sep. 1; 25(17): 3389-402, accessible through the home page of the NCBI at www.ncbi.nlm.nih.gov) and FASTA (Pearson W R, Methods Enzymol. 1990; 183:63-98. Pearson J Mol. Biol. 1998 Feb. 13; 276(1): 71-84).

Muteins of the polypeptide of the invention, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of the polypeptide of the invention may include synonymous amino acids within a group which have sufficiently similar physicochemical properties that substitution between members of the group will preserve the biological function of the molecule (Grantham Science. 1974 Sep. 6; 185(4154): 862-4). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |

TABLE 2-continued

More Preferred Groups of Synonymous Amino Acids

| Amino Acid | Synonymous Group |
|---|---|
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of the polypeptide of the invention, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

"Functional derivatives" as used herein cover derivatives of the polypeptide of the invention, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of the polypeptide of the invention, and do not confer toxic properties on compositions containing it.

"Functional derivatives" also comprise multimers made up of the polypeptide of the invention in which changes have been introduced in the sequence of the amino acids making up the polypeptide of the invention by any conventional method. These changes may comprise elongation or truncation of the polypeptide of the invention or deletion or replacement of one or more amino acids making up the polypeptide of the invention. It is understood that none of the above changes may affect the properties of the polypeptide of the invention.

These derivatives may, for example, include polyethylene glycol side-chains, which may mask antigenic sites and extend the residence of the polypeptide of the invention in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of the 13 kDa or 16 kDa fragments. The term fragment refers to any subset of the molecule, that is, a shorter peptide that retains the desired biological activity e.g. inducing TNF secretion by IL-32 responsive cells. Fragments may readily be prepared by removing amino acids from either end of the polypeptide of the invention and testing the resultant fragment for its biological properties. Proteases for removing one amino acid at a time from either the N-terminal or the C-terminal of a polypeptide are known, and so determining fragments, which retain the desired biological activity, involves only routine experimentation.

As active fractions of the polypeptide of the invention, muteins and fused proteins thereof, the present invention further covers any fragment of the polypeptide chain of the protein molecule alone or together with associated molecules or residues linked thereto, e.g., sugar or phosphate residues, or aggregates of the protein molecule or the sugar residues by themselves, provided said fraction has substantially similar activity to the polypeptide of the invention.

In yet a further embodiment, the substance according to the invention comprises an immunoglobulin fusion, i.e. the molecules according to the invention are fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the polypeptide of the invention. The resulting fusion protein ideally has improved properties, such as an extended residence time in body fluids (half-life), increased specific activity, increased expression level, or facilitated purification of the fusion protein.

Preferably, the substance according to the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero- or homomultimeric.

The term "salts" herein refers to both salts of carboxyl groups and to acid addition salts of amino groups of the polypeptide of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the polypeptide of the invention such as the ability to induce TNF, IL-8 or MIP-2 in IL-32 responsive cells.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Circularly permuted molecules, which may include DNA, RNA and protein, are single-chain molecules, which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

The invention provides a pharmaceutical composition comprising the polypeptide fragment of IL-32 of about 16 kDa or of about 13 kDa and a pharmaceutically acceptable carrier.

The invention provides also a pharmaceutical composition comprising the polypeptide fragment of IL-32 of about 16 kDa or of about 13 kDa and a pharmaceutically acceptable carrier for the treatment of a disease induced by a pathogen.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The present invention relates to a method of enhancing immunity in a patient in need, e.g. a patient suffering from an infectious disease and cancer, comprising administration of a therapeutically effective amount of said fragment of IL-32.

A "therapeutically effective amount" is such that when administered, said fragment of IL-32 results in enhancement of host defense. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the activity said IL-32 fragments.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The present invention will now be described in more detail in the following non-limiting examples and the accompanying drawings.

EXAMPLES

Example 1

Isolation of an IL-32 Binding Protein from Human Urinary Proteins

An affinity column of human recombinant IL-32 (hrIL-32) was prepared in order to isolate IL-32 binding proteins from human urine.

A recombinant human IL-32α (3 mg) produced in *E. coli* was coupled to Affigel-15 (1 ml, BioRad, Richmond Calif.), according to the manufacturer's instructions and packed into a column. A 1000-fold concentrate of human crude urinary proteins (500 ml) was loaded onto the column at a flow rate of 0.25 ml/min. The column was washed with 250 ml of a solution containing 0.5 M NaCl in phosphate buffered saline (PBS). Column-bound proteins were eluted with a solution containing 25 mM citric acid, pH 2.2 and benzamidine (1 mM) and 1 ml fractions were collected and neutralized immediately by 1 M $Na_2CO_3$ (0-70 microliters. For Elution 3, 70 microliters of neutralizing solution were used). Aliquots of the fractions eluted from the column (and of the wash fraction) were resolved by SDS-PAGE (10%) under non-reducing conditions and the protein bands were visualized by silver staining. A broad band corresponding to a specific IL-32 binding protein of 28-32 kDa was detected mainly in eluted fraction 3 (arrow in FIG. 1). This band was not seen in the wash fraction, which represents crude urinary proteins.

The results show that a fraction of urinary proteins enriched with an IL-32 binding protein of 28-32 kDa was obtained by affinity chromatography with a column of hrIL-32.

Example 2

Identification of IL-32 Binding Protein as Proteinase 3

The following experiment was carried out in order to identify the urinary IL-32 binding protein enriched by affinity chromatography with the hrIL-32 column (Example 1).

The band from the SDS-PAGE from Example 1, corresponding to 28-32 kDa was excised from the gel and the proteins were electro-eluted and digested with trypsin. The resulting tryptic digest was subjected to liquid-chromatography and tandem mass spectrometry (LC-MS/MS). The sequence of three tryptic peptides was unequivocally determined as being: LFPDFFTR, VALYVDWIR and LVNVVLGAHNVR. Alignment of the sequence of the three tryptic peptides and tryptic peptides sequences in the protein database of the National Center for Biotechnology Information (NCBI) at the National Institute of Health, Bethesda Md., revealed that the IL-32 binding protein isolated by affinity chromatography is the human Proteinase-3 (PR-3, SwissProt Accession No P24158). An additional protein corresponding to human immunoglobulin chain was also identified in the same protein band but it appears to be a non-specific component.

That IL-32 binding protein is PR-3 was further confirmed by N-terminal protein microsequence analysis. The 28-32 kDa protein band of the SDS-PAGE of elution fraction 3 (Example 1 and FIG. 1) was excised from the gel, electroeluted onto a PVDF membrane according to the manufacturer's instruction, and subjected to protein microsequencing on a Model Applied Biosystems instrument. The resulting N-terminal sequence of the electroeluted 28-32 kDa protein was identical to that of the commercially available PR-3 (Athens Research and Technology), IVGG. This sequence is present in positions 28-31 of pro-PR-3.

The results show that the urinary IL-32-binding-protein of 28-32 kDa, which was isolated by affinity purification, is PR-3.

Example 3

Affinity of Binding of PR-3 to IL-32

The binding affinity of PR-3 (from urine or commercially available) to IL-32 was measured by surface plasmon resonance (BIAcore).

Figure 2:
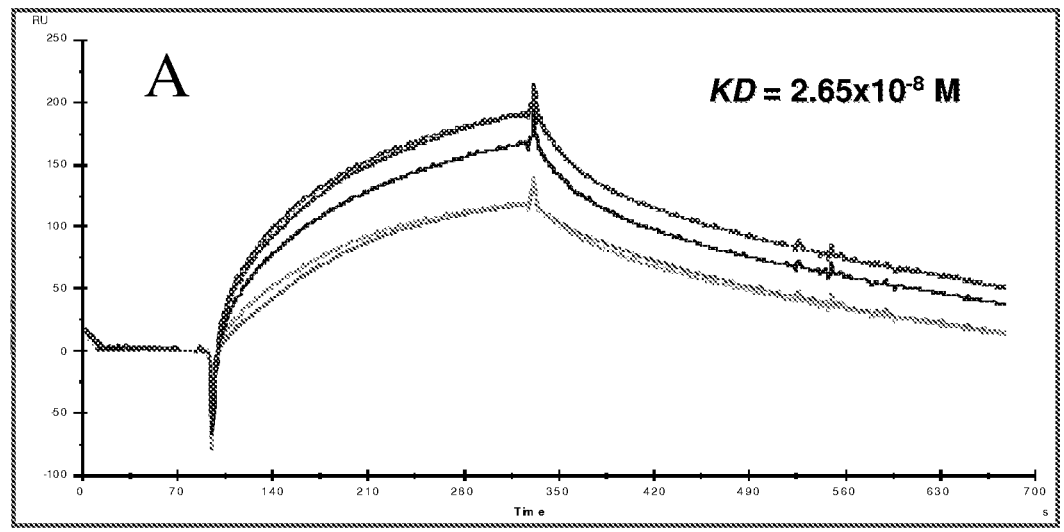
FIG. 2 A-B shows kinetics of human urinary PR-3 binding to human IL-32 as measured by surface plasmon resonance.
Figure 2:
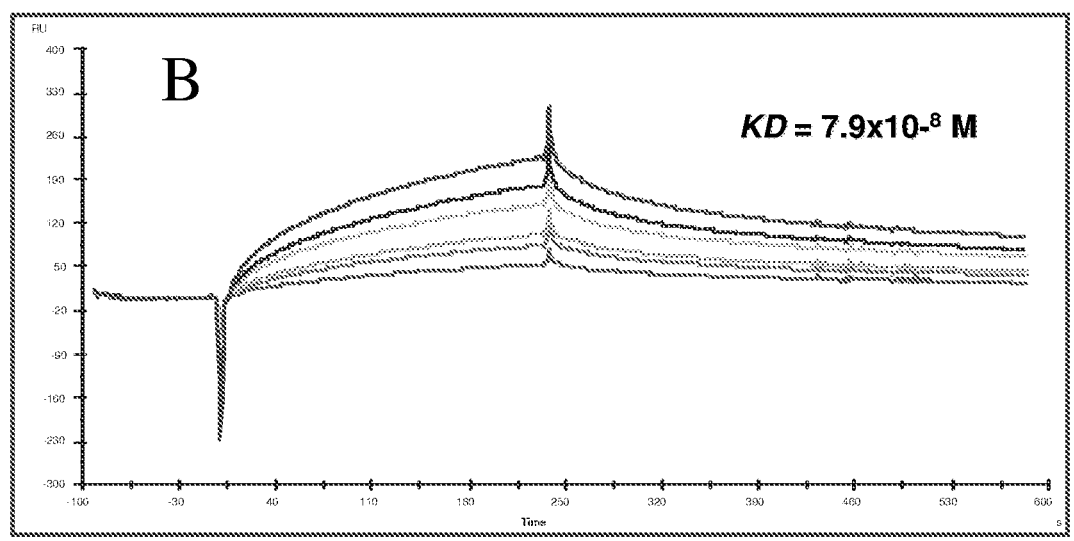
Figure 3:
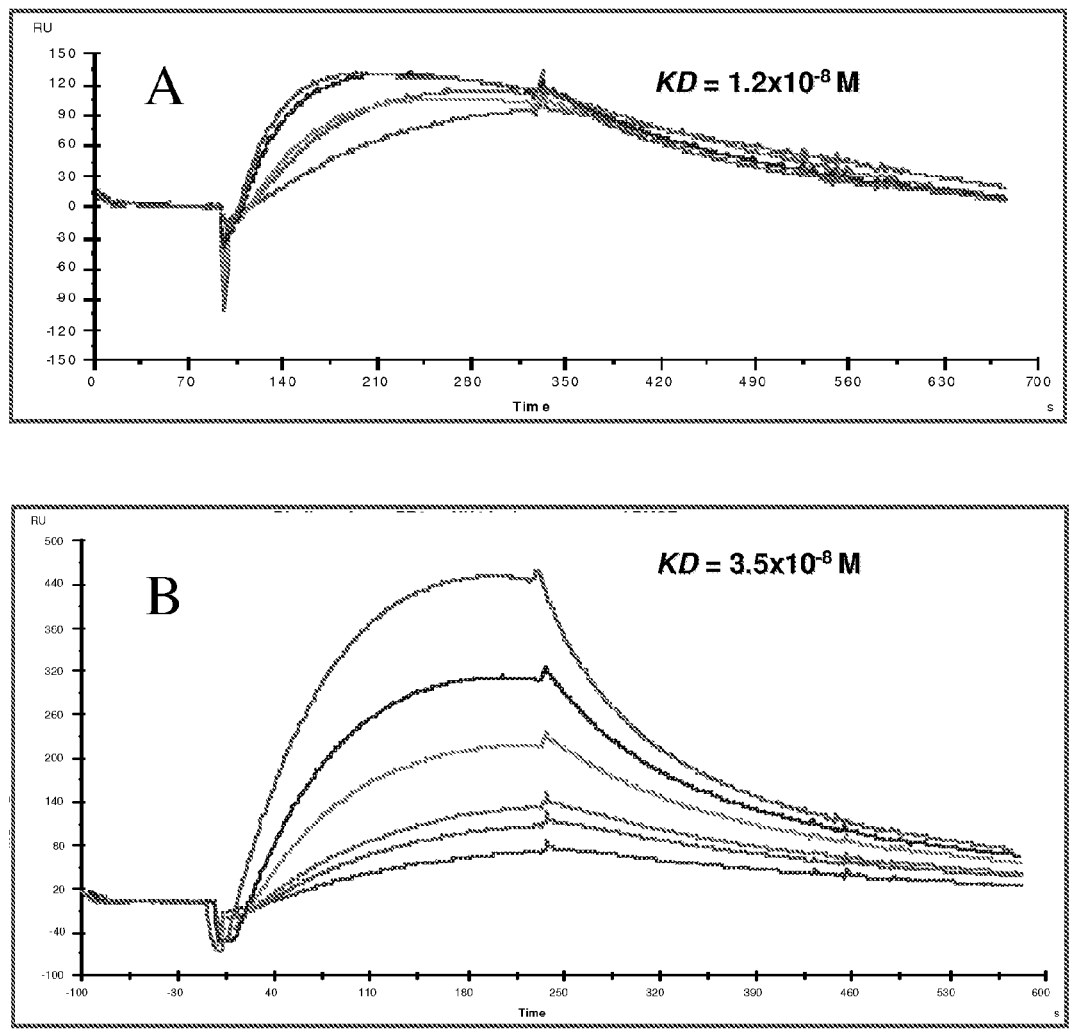
FIG. 3 A-B shows kinetics of commercially available human PR-3 binding to human IL-32 as measured by surface plasmon resonance. For details see FIG. 2. The binding data gave a kD of $1.2 \times 10^{-8}$ M with active PR-3, which considerably degraded the immobilized IL-32 (FIG. 3 A). The kD of commercially available PR-3 that was inactivated by PMSF (FIG. 3 B) was $3.5 \times 10^{-8}$ M.

IL-32 (20 μg/ml) in acetate buffer pH 4.6) was immobilized to a single channel of a BIAcore chip as recommended by the manufacturer (Amersham Pharmacia, Uppsala Sweden). Aliquots of elution fraction 3 from the IL-32 affinity column containing urinary PR3, were brought to a concentration of 10, 20, 30, 40 and 80 nM and analyzed by the BIAcore system. The binding data gave a kD of $2.65 \times 10^{-8}$ M. (FIG. 2A). The same analysis was done with PR-3 that was inactivated by PMSF (1 mM) (FIG. 2B). The resulting kD was $7.9 \times 10^{-8}$ M. The same analysis was done with a commercially available human neutrophil derived PR-3 (Athens Research and Technology, Athens Ga., 0.5 μg in 20 μl gelatin solution) (FIG. 3A). The resulting kD was $1.2 \times 10^{-8}$ M. The binding was repeated with commercial PR-3 that was inactivated by PMSF (FIG. 3B). The resulting kD was $3.5 \times 10^{-8}$ M.

The chip could not be re-used indicating that IL-32 is being cleaved from the chip by PR3.

The results obtained show that binding of IL-32 to PR-3 is not dependent on the enzymatic activity of the latter, since PR-3 pre incubated with PMSF still binds to the IL-32 with high affinity.

Example 4

Radioactive Labeling of IL-32

The preceding example shows that IL-32 is a substrate for PR-3. In order to explore the catalytic activity of PR-3 on IL-32 degradation, radioactive labeled IL-32 was prepared as follows.

IL-32 (15 μg in 60 μl phosphate buffer pH 7.4) was iodinated using the modification of the Chloramine T method. Briefly, a mixture of Chloramine T (50 μl, 1 mg/ml in $H_2O$) and 1 mCi [$^{125}$I]-NaI (10 μl) was incubated for 20 sec at 4° C. and was added to the IL-32 preparation for additional 20 sec at 4° C. The reaction was stopped by the addition of sodium meta bisulfite (50 μl of a stock of 5 mg/ml) and potassium iodide (50 μl of a stock of 5 mg/ml). Radioactive labeled IL-32 was separated from free iodine on Sephadex G25 column (Pharmacia), which was first equilibrated with 0.25% gelatin in PBS containing 0.025% sodium azide (i.e. gelatin solution). Six 1 ml fractions were collected using the gelatin solution. Fractions 3 and 4 contained the peak of the labeled of $^{125}$I-IL-32 (specific activity ~$2 \times 10^5$ cpm/ng).

Example 5

Kinetics of Degradation of $^{125}$I-IL-32 by Urinary PR-3

The following experiment was carried out in order to explore the kinetic of IL-32 degradation by PR-3.

Figure 4:
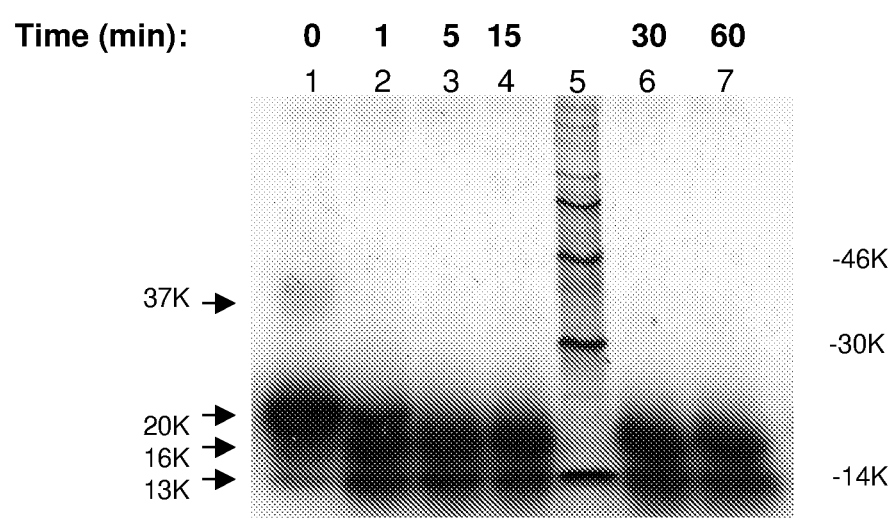
FIG. 4 shows the kinetics of digestion of $^{125}$I-IL-32 by urinary PR-3. Lane 1 shows the resolved undigested $^{125}$I-IL-32, Lane 5 the molecular weight markers (in kDa see the right side of the FIG.) and lanes 2-4 and 6-7 show $^{125}$I-IL-32 following incubation with PR-3 for 1, 5, 15, 30 and 60 minutes at 37° C., respectively. After 1 minute of incubation with PR-3 the 20 kDa IL-32 (Lane 1) was cleaved into two cleavage products of 16 and 13 kDa (Lane 2). After 5 min. (Lane 3) the band corresponding to the intact IL-32 disappeared and the cleavage products remained stable for at least 60 min. (lanes 3, 4, 6, and 7). The resulting $^{125}$I-IL-32 fragments of apparent MW of 20 kDa, 16 kDa and 13 kDa are indicated on the left side of the FIG.

Affinity purified urinary PR-3 (elution 3 fraction from Example 1, FIG. 1, 50 μl) was added to $^{125}$I-IL-32 (250,000 cpm in 10 μl of gelatin solution) and incubated at 37° C. for 0, 1, 5, 15, 30, and 60 min. (FIG. 4). Degradation was stopped by the addition of SDS-PAGE sample buffer and by boiling for 10 min. Samples containing $^{125}$I-IL-32 and PR-3 incubated at different periods of time (0-60 min.) were resolved on 12% SDS-PAGE under reducing conditions. The gel was dried and autoradiographed. The results summarized on FIG. 4 show the reduction in the 20 kDa band representing intact IL-32 (FIG. 4, lane 1) and the increase in the levels of a 16 and 13 kDa IL-32 cleavage products after a 1-minute incubation with PR-3 (FIG. 4, lane 2). It was found that the 20 kDa band completely disappeared and the levels of the 16 and 13 kDa IL-32 cleavage products increased after a 5 min. incubation with PR-3 (lane 3) and that the high levels of the 16 and 13 kDa IL-32 fragments remained stable for up to 60 min (FIG. 4, lanes 3, 4, 6, and 7).

We found that incubation of IL-32 with PR-3 overnight at 4° C. resulted in a complete digestion and no product higher than the 10 kDa marker (the limit of the gel) was observed (data not shown).

Example 6

Kinetics of Cleavage of $^{125}$I-IL-32 by Urinary and Commercial PR-3

Figure 5:
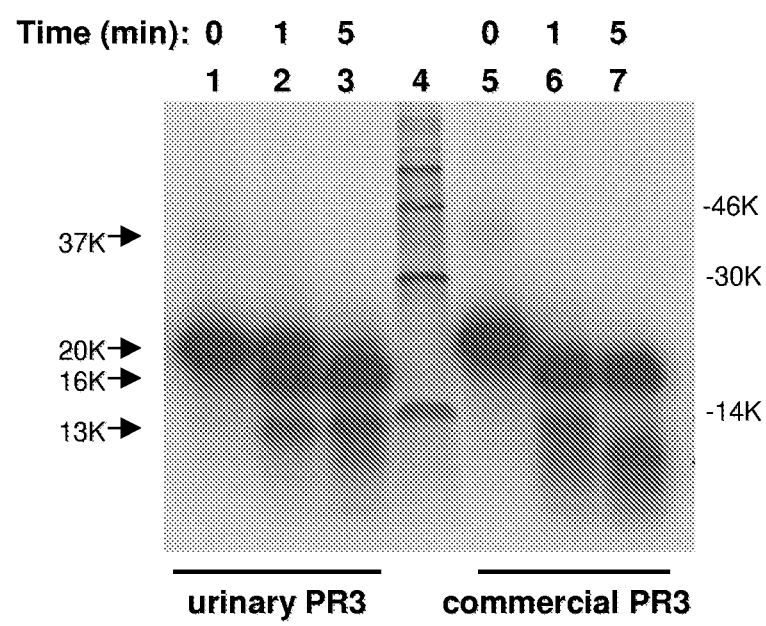
FIG. 5 shows the comparison of IL-32 cleavage by urinary and commercial PR-3. The experiment was carried out essentially as indicated in FIG. 4 (Example 5) except, that incubation of PR-3 and IL32 was limited to up to 5 minutes and that both urinary and commercial PR-3 were used. Urinary (Lines 1-3) or commercial PR-3 (Lines 5-7) were incubated with $^{125}$I-IL-32 for 0, 1 and 5 minutes. The results show that commercial PR-3 was more efficient than the urine-derived PR-3 since the 20 kDa IL-32 was completely cleaved into its 16 and 13 kDa fragments after 1 min (compare lanes 6 and 2).

The experiment presented in FIG. 5 was carried out essentially as described in example 5, except that it was limited to up to five-minute incubation of IL-32 with either urinary or commercial PR-3.

Urinary PR-3 or commercial PR-3 (Athens Research and Technology) were incubated with $^{125}$I-IL-32 for 0, 1 and 5 min. Digestion was stopped by the addition of SDS-PAGE sample buffer and by boiling for 10 min. The samples were resolved on SDS-PAGE under reducing conditions. The gel was dried and autoradiographed. The results summarized on FIG. 5 show that the commercial PR-3 is more potent than the urinary PR-3, leading to complete disappearance of the 20 kDa IL-32 band within 1 min (compare lane 6 with lane 2). This difference is probably due to a different specific activity of urinary vs. commercial PR3.

Example 7

Inhibition of the Proteolytic Activity of PR-3 by Phenyl Methyl Sulfonyl Fluoride (PMSF)—A General Serine Protease Inhibitor The following experiment was carried out to prove that the degradation of following incubation with PR-3 is due to the proteolytic activity of PR-3.

Figure 6:
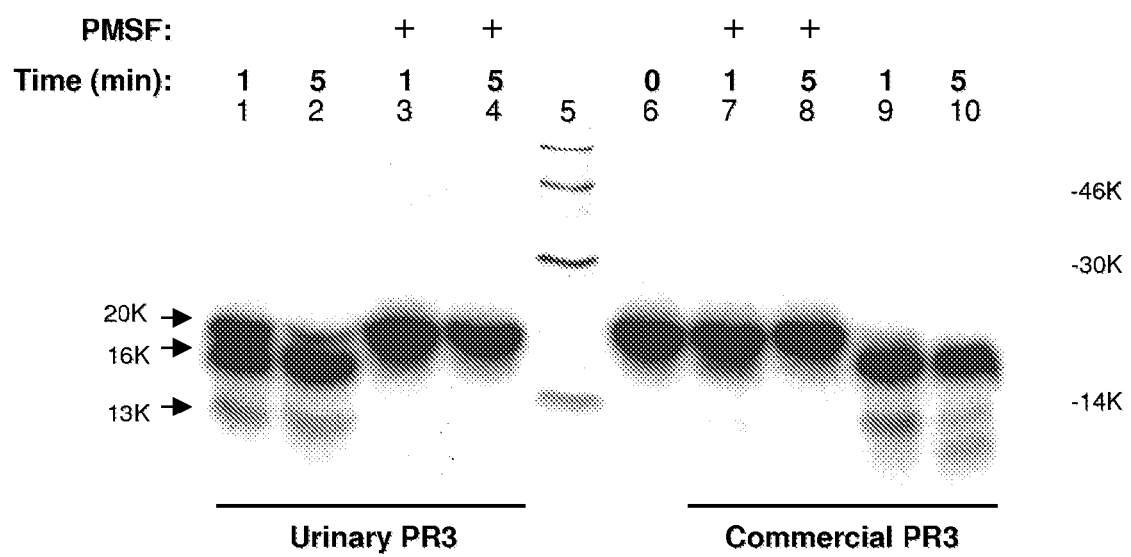
FIG. 6 shows that phenyl methyl sulfonyl fluoride (PMSF), a serine protease inhibitor, blocks the enzymatic activity of both urinary and commercial PR3 and blocks the cleavage of IL-32. Lanes 1-4 show $^{125}$I-IL-32 following incubation with urinary PR-3 for 1 and 5 min., either not treated (Lanes 1 and 2) or pre-treated with PMSF (Lanes 3 and 4). Lanes 7-10 show $^{125}$I-IL-32 following incubation with commercial PR-3 for 1 and 5 min., either not treated (Lanes 9 and 10) or pre-treated with PMSF (Lanes 7 and 8). Molecular weight markers (in kDa; lane 5) are indicated at the right side. Lane 6 shows undigested $^{125}$I-IL-32. The figure shows the extent of cleavage of IL-32 by urinary and commercial PR-3 after 1 and 5 min. of incubation (lanes 1 and 5 for urinary and 9 and 10 for commercial) and that PMSF completely blocked IL-32 cleavage by both commercial and urinary PR-3.

The experiment presented in FIG. 6 was performed as described in examples 5 and 6, except that PR-3 was pre-incubated with PMSF (final concentration of 1 mM, 10 min at 37° C.) prior to the incubation with $^{125}$I-IL-32. PMSF completely abolished the ability of urinary and commercial PR-3 to process IL-32. In contrast to active PR-3 (lane 1,2 and 9,10 for urinary and commercial PR-3, respectively), no cleavage products were observed with PMSF pretreated PR-3 incubated with IL-32 (FIG. 6, lanes 3, 4, 7, 8).

Example 8

The Effect of PR-3 in the Activity of IL-32

The results obtained in the preceding examples show that PR-3 binds with high affinity to IL-32 and cleaves IL-32 within minutes. The following experiments were carried out to explore the effect of PR-3 on the biological activity of IL-32.

Figure 7:
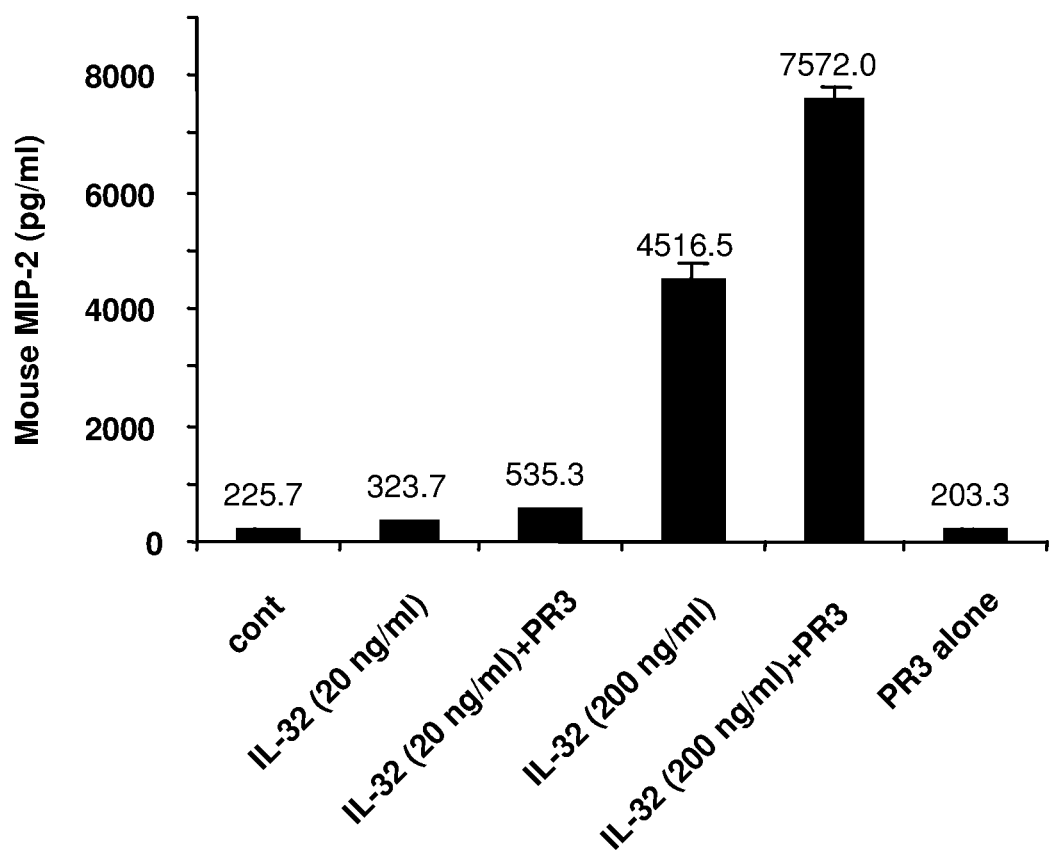
FIG. 7 shows enhanced biological activity of IL-32 pretreated with PR-3 in mouse Raw 264.7 cells. Mouse macrophage Raw 264.7 cell line were seeded in a 96 well plate and incubated with IL-32 (20 or 200 ng/ml), IL-32 pretreated with PR-3 (100 ng/ml) for 5 min. or with PR-3 alone as the a control, and MIP-2 secreted into the cell culture medium was measured. The results summarized in the FIG. show that IL-32 induced the secretion of MIP-2 by Raw 264.7 cells and that preincubation of IL-32 with PR-3 for 5 minutes prior to treatment of the cells (shown in FIGS. 4-6 to cleave the 20 kDa IL-32 into 16 and 13 kDa fragments) enhanced MIP-2 secretion. PR-3 alone had no effect on the cells.

Mouse macrophage Raw 264.7 cell line (American Type Culture Collection, ATCC) was maintained in RPMI-1640 medium containing 10% FCS. Bioassays were performed in 96 well plates. Briefly, Raw cells ($5 \times 10^5$/ml, 0.1 ml/per well) were seeded and cultured until cells adhered to the plate. The medium was removed and the cells were then stimulated with fresh medium (without FCS) containing different concentration of IL-32 or IL-32 pre-treated with PR-3 for 5 min at room temperature in the presence 5 µg/ml of the LPS blocker polymyxin B (Bedford Laboratories, Bedford, Ohio). The plates were incubated at 37° C. with 5% $CO_2$ for 16-20 h and then the culture supernatants were collected to measure MIP-2 released by the cell culture. The results are summarized in FIG. 7 and show that PR-3-pretreated IL-32 enhances the production of MIP-2 in Raw 264.7 cells compared to non-pretreated IL-32.

Figure 8:
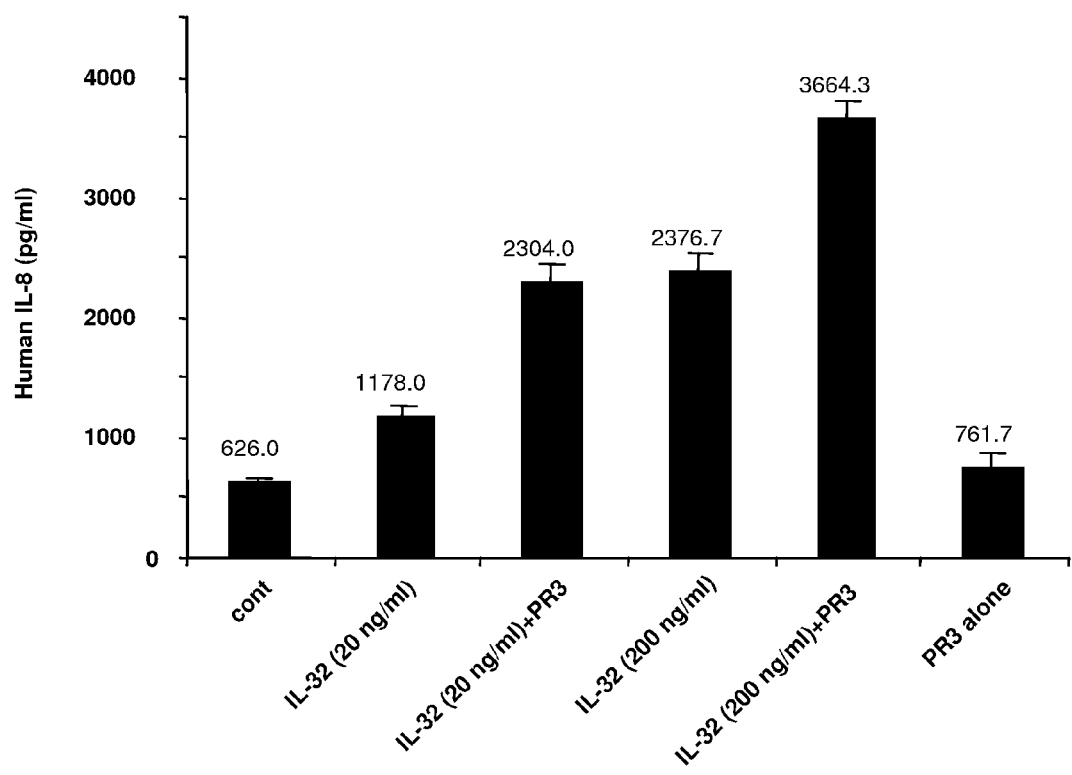
FIG. 8 shows enhanced biological activity of IL-32 pretreated with PR-3 in human peripheral blood mononuclear cells (PBMC). Human PBMC cells were seeded in 96 well plates and incubated with IL-32 (20 or 200 ng/ml), IL-32 pretreated with PR-3 (100 ng/ml) for 5 min. or with PR-3 alone as the a control. The content of IL-8 into the cell culture medium was measured. The results show that IL-32 induced the secretion of IL-8 in human PBMC cells and that incubation of IL-32 for 5 minutes with PR-3 (shown to induce complete IL-32 degradation in FIGS. 4-6) prior to cell treatment enhanced IL-8 secretion. Incubation of the cells with PR-3 alone did not induce IL-8 in the mouse cells.

Similar enhancement of IL-32 activity by pre-treatment with PR-3 was shown in an experiment carried out with human peripheral blood mononuclear cells (PBMC). PBMC were prepared as previously described [Kim, 2005 #36] and seeded at a concentration of $5 \times 10^5$ cells per well in 96 well plates. The experimental setting of stimulation with IL-32 and IL-32 pre treated with PR-3 was identical to that described above for the mouse Raw cells. After stimulation of the human PBMC cells with either IL-32 or IL-32 pre treated with PR-3, the culture supernatants were collected to measure human IL-8 released by the cells. The results are summarized in FIG. 8 and show that stimulation with PR-3-pre-treated IL-32 enhances the production of IL-8 in human PBMC cells compared to non-pretreated IL-32.

Example 9

PR-3 Fragment Preparation and Activity

PR3 (Sigma) was reduced and alkylated prior to cleavage by CNBr. Reduction and alkylation: DTT (18 µl 50 mM) was added to a PR3 sample (90 µg, 1 mg/ml) and incubated for 1 hour at 56° C. Iodoacetamide (60 µl, 100 mM) was added and the mixture was incubated for 45 min at room temperature in the dark. The reaction was stopped by DTT (33.6 µl, 50 mM). The sample was dried and reconstituted in 70 µl formic acid. Solid Cyanogen Bromide (CNBr) was added for 48 hrs at room temperature and in the dark. CNBr desalting was done with C18 Zip-tip according to manufacturer instructions. The peptides mixture was subjected to mass spectrometry (Maldi) which showed formation of two peptides.

Another sample of PR3 is reduced, alkylated and cleaved by CNBr. The resulting peptides are separated by RP-HPLC (Sigma Discovery BIO Wide Pore C8 HPLC column, 5 µm particle size, 5 cm×4 mm). Since mature PR-3 has three methionines, up to four peptides are expected to be formed by the CNBr cleavage: the N-terminal 1678 Kda peptide, a 549 and a 11712 Kda peptide, and a C-terminal 11187 Kda peptide.

The affinity of each peptide to IL-32 is determined by BIACORE compared to the affinity of intact enzymatically active PR3 to IL32 and to the affinity of intact enzymatically non-active PR-3 to IL-32.

The peptides are then tested for inhibition of the biological activity of IL-32.

REFERENCES

1. Adkison, A. M., et al., Dipeptidyl peptidase I activates neutrophil-derived serine proteases and regulates the development of acute experimental arthritis. J Clin Invest, 2002. 109(3): p. 363-71.
2. Baggiolini, M., et al., The polymorphonuclear leukocyte. Agents Actions, 1978. 8(1-2): p. 3-10.
3. Berger, S. P., et al., Proteinase 3, the major autoantigen of Wegener's granulomatosis, enhances IL-8 production by endothelial cells in vitro. J Am Soc Nephrol, 1996. 7(5): p. 694-701.
4. Cadene, M., et al., Inhibition of neutrophil serine proteinases by suramin. J Biol Chem, 1997. 272(15): p. 9950-5.
5. Coeshott, C., et al., Converting enzyme-independent release of tumor necrosis factor alpha and IL-1beta from a stimulated human monocytic cell line in the presence of activated neutrophils or purified proteinase 3. Proc Natl Acad Sci USA, 1999. 96(11): p. 6261-6.
6. Cooley, J., et al., The serpin MNEI inhibits elastase-like and chymotrypsin-like serine proteases through efficient reactions at two active sites. Biochemistry, 2001. 40(51): p. 15762-70.
7. Csernok, E., et al., Transforming growth factor-beta (TGF-beta) expression and interaction with proteinase 3 (PR-3) in anti-neutrophil cytoplasmic antibody (ANCA)-associated vasculitis. Clin Exp Immunol, 1996. 105(1): p. 104-11.
8. Dahl, C. A., et al., Identification of a novel gene expressed in activated natural killer cells and T cells. J Immunol, 1992. 148(2): p. 597-603.
9. Date, K., et al., HGF/NK4 is a specific antagonist for pleiotrophic actions of hepatocyte growth factor. FEBS Lett, 1997. 420(1): p. 1-6.
10. Frosch, M. and D. Foell, Wegener granulomatosis in childhood and adolescence. Eur J Pediatr, 2004. 163(8): p. 425-34.
11. Groutas, W. C., et al., Inhibition of human leukocyte proteinase 3 by a novel recombinant serine proteinase inhibitor (LEX032). Biochem Biophys Res Commun, 1997. 233(3): p. 697-9.
12. Groutas, W. C., et al., Structure-based design of a general class of mechanism-based inhibitors of the serine proteinases employing a novel amino acid-derived heterocyclic scaffold. Biochemistry, 1997. 36(16): p. 4739-50.
13. Jennette, J. C. and R. J. Falk, Small-vessel vasculitis. N Engl J Med, 1997. 337(21): p. 1512-23.
14. Just, J., et al., Proteinase 3 mRNA expression is induced in monocytes but not in neutrophils of patients with cystic fibrosis. FEBS Lett, 1999. 457(3): p. 437-40.
15. Kam, C. M., et al., Substrate and inhibitor studies on proteinase 3. FEBS Lett, 1992. 297(1-2): p. 119-23.
16. Kao, R. C., et al., Proteinase 3. A distinct human polymorphonuclear leukocyte proteinase that produces emphysema in hamsters. J Clin Invest, 1988. 82(6): p. 1963-73.
17. Kim, S. H., et al., Interleukin-32: a cytokine and inducer of TNFalpha. Immunity, 2005. 22(1): p. 131-42.
18. Kim, Y. and M. Nirenberg, Drosophila NK-homeobox genes. Proc Natl Acad Sci USA, 1989. 86(20): p. 7716-20.
19. Lamprecht, P. and W. L. Gross, Wegener's granulomatosis. Herz, 2004. 29(1): p. 47-56.
20. Muller Kobold, A. C., C. G. Kallenberg, and J. W. Tervaert, Leucocyte membrane expression of proteinase 3 correlates with disease activity in patients with Wegener's granulomatosis. Br J Rheumatol, 1998. 37(8): p. 901-7.

21. Ohlsson, S., et al., Increased expression of the secretory leukocyte proteinase inhibitor in Wegener's granulomatosis. Clin Exp Immunol, 2003. 131(1): p. 190-6.
22. Padrines, M., et al., Interleukin-8 processing by neutrophil elastase, cathepsin G and proteinase-3. FEBS Lett, 1994. 352(2): p. 231-5.
23. Panelli, M. C., et al., Gene-expression profiling of the response of peripheral blood mononuclear cells and melanoma metastases to systemic IL-2 administration. Genome Biol, 2002. 3(7): p. RESEARCH0035.
24. Pendergraft, W. F., 3rd, et al., Proteinase 3 sidesteps caspases and cleaves p21(Waf1/Cip1/Sdi1) to induce endothelial cell apoptosis. Kidney Int, 2004. 65(1): p. 75-84.
25. Preston, G. A., et al., Novel effects of neutrophil-derived proteinase 3 and elastase on the vascular endothelium involve in vivo cleavage of NF-kappaB and proapoptotic changes in JNK, ERK, and p38 MAPK signaling pathways. J Am Soc Nephrol, 2002. 13(12): p. 2840-9.
26. Ramaha, A. and P. A. Patston, Release and degradation of angiotensin I and angiotensin II from angiotensinogen by neutrophil serine proteinases. Arch Biochem Biophys, 2002. 397(1): p. 77-83.
27. Robache-Gallea, S., et al., In vitro processing of human tumor necrosis factor-alpha. J Biol Chem, 1995. 270(40): p. 23688-92.
28. Skold, S., et al., A secreted proform of neutrophil proteinase 3 regulates the proliferation of granulopoietic progenitor cells. Blood, 1999. 93(3): p. 849-56.
29. Smart, Y. C., et al., Expression of natural killer (NK) cell-specific alloantigens on a mouse NK-like cell line. Immunol Cell Biol, 1989. 67 (Pt 4): p. 239-42.
30. Uehara, A., et al., Proinflammatory cytokines induce proteinase 3 as membrane-bound and secretory forms in human oral epithelial cells and antibodies to proteinase 3 activate the cells through protease-activated receptor-2. J Immunol, 2004. 173(6): p. 4179-89.
31. van Ros sum, A. P., P. C. Limburg, and C. G. Kallenberg, Membrane proteinase 3 expression on resting neutrophils as a pathogenic factor in PR-3-ANCA-associated vasculitis. Clin Exp Rheumatol, 2003. 21(6 Suppl 32): p. S64-8.
32. von Bredow, C., A. Wiesener, and M. Griese, Proteolysis of surfactant protein D by cystic fibrosis relevant proteases. Lung, 2003. 181(2): p. 79-88.
33. Wiedow, O., J. Luademann, and B. Utecht, Elafin is a potent inhibitor of proteinase 3. Biochem Biophys Res Commun, 1991. 174(1): p. 6-10.
34. Witko-Sarsat, V., et al., A large subset of neutrophils expressing membrane proteinase 3 is a risk factor for vasculitis and rheumatoid arthritis. J Am Soc Nephrol, 1999. 10(6): p. 1224-33.
35. Yang, J. J., et al., Circumvention of normal constraints on granule protein gene expression in peripheral blood neutrophils and monocytes of patients with antineutrophil cytoplasmic autoantibody-associated glomerulonephritis. J Am Soc Nephrol, 2004. 15(8): p. 2103-14.
36. Yang, J. J., et al., Expression profile of leukocyte genes activated by anti-neutrophil cytoplasmic autoantibodies (ANCA). Kidney Int, 2002. 62(5): p. 1638-49.
37. Yang, J. J., et al., Internalization of proteinase 3 is concomitant with endothelial cell apoptosis and internalization of myeloperoxidase with generation of intracellular oxidants. Am J Pathol, 2001. 158(2): p. 581-92.
38. Zani, M. L., et al., Kinetics of the inhibition of neutrophil proteinases by recombinant elafin and pre-elafin (trappin-2) expressed in *Pichia pastoris*. Eur J Biochem, 2004. 271(12): p. 2370-8

The above-cited references and those reference cited throughout the specification are herein incorporated by reference in their entirety.

---

The invention claimed is:

1. A method of screening for an inhibitor of activation of interleukin 32 (IL-32) based on the proteolytic activity of proteinase 3 (PR-3) on IL-32, the method comprising the steps of
    (a) contacting a composition comprising an IL-32 with protein PR3 in the presence of a test agent;
    (b) detecting the presence of an IL-32 proteolytic fragment; and
    (c) identifying the test agent as the inhibitor of activation of IL-32 when the presence of the proteolytic fragment is less and when presence of the intact IL-32 protein is more than that in a control without the test agent.

2. The method of claim 1, wherein the detection is performed using SDS-PAGE.

3. The method according to claim 1, wherein the intact IL-32 protein is about 20 kDa and wherein said IL-32 proteolytic fragment is about 16 kDa.

4. The method according to claim 1, wherein the intact IL-32 protein is about 20 kDa and wherein said IL-32 proteolytic fragment is about 13 kDa.

5. The method of claim 1, further comprising assaying the inhibiting effect of the identified inhibitor of activation of IL-32 in IL-32 induced secretion of a cytokine, which comprises contacting the IL-32 composition and PR-3 with IL-32 responsive T-cell or macrophage cell in a culture medium in the presence of the inhibitor, measuring a cytokine concentration in the culture medium, and comparing the cytokine concentration in the culture medium to the cytokine concentration in a control culture medium absent said inhibitor, wherein lower cytokine concentration is detected in the culture medium comprising the inhibitor as compared to the control.

6. The method of claim 5 wherein the cytokine is selected from tumor necrosis factor alpha, Interleukin-8, and macrophage inflammatory protein-2.

* * * * *

SEQUENCE LISTING

```
<160> NUMBER OF SEQ ID NOS: 6

<210> SEQ ID NO 1
<211> LENGTH: 57
<212> TYPE: PRT
<213> ORGANISM: Homo sapiens

<400> SEQUENCE: 1

Met Cys Phe Pro Lys Val Leu Ser Asp Asp Met Lys Lys Leu Lys Ala
1               5                   10                  15

Arg Met His Gln Ala Ile Glu Arg Phe Tyr Asp Lys Met Gln Asn Ala
            20                  25                  30

Glu Ser Gly Arg Gly Gln Val Met Ser Ser Leu Ala Glu Leu Glu Asp
        35                  40                  45

Asp Phe Lys Glu Gly Tyr Leu Glu Thr
    50                  55

<210> SEQ ID NO 2
<211> LENGTH: 74
<212> TYPE: PRT
<213> ORGANISM: Homo sapiens

<400> SEQUENCE: 2

Val Ala Ala Tyr Tyr Glu Glu Gln His Pro Glu Leu Thr Pro Leu Leu
1               5                   10                  15

Glu Lys Glu Arg Asp Gly Leu Arg Cys Arg Gly Asn Arg Ser Pro Val
```

```
                        20                  25                  30
Pro Asp Val Glu Asp Pro Ala Thr Glu Glu Pro Gly Glu Ser Phe Cys
                35                  40                  45

Asp Lys Ser Tyr Gly Ala Pro Arg Gly Asp Lys Glu Glu Leu Thr Pro
        50                  55                  60

Gln Lys Cys Ser Glu Pro Gln Ser Ser Lys
65                  70

<210> SEQ ID NO 3
<211> LENGTH: 8
<212> TYPE: PRT
<213> ORGANISM: Homo sapiens

<400> SEQUENCE: 3

Tyr Leu Glu Thr Val Ala Ala Tyr
1               5

<210> SEQ ID NO 4
<211> LENGTH: 8
<212> TYPE: PRT
<213> ORGANISM: Homo sapiens

<400> SEQUENCE: 4

Leu Phe Pro Asp Phe Phe Thr Arg
1               5

<210> SEQ ID NO 5
<211> LENGTH: 9
<212> TYPE: PRT
<213> ORGANISM: Homo sapiens

<400> SEQUENCE: 5

Val Ala Leu Tyr Val Asp Trp Ile Arg
1               5

<210> SEQ ID NO 6
<211> LENGTH: 12
<212> TYPE: PRT
<213> ORGANISM: Homo sapiens

<400> SEQUENCE: 6

Leu Val Asn Val Val Leu Gly Ala His Asn Val Arg
1               5                   10
```